United States Patent [19]
Nakamura et al.

[11] Patent Number: 5,927,815
[45] Date of Patent: Jul. 27, 1999

[54] BALANCING CHAIR

[75] Inventors: Katsushige Nakamura, Tokyo; Tomio Ota, Osaka, both of Japan

[73] Assignee: Mitaka Kohki Co., Ltd., Tokyo, Japan

[21] Appl. No.: 09/049,280

[22] Filed: Mar. 26, 1998

[30] Foreign Application Priority Data

Mar. 31, 1997 [JP] Japan ..................................... 9-080175

[51] Int. Cl.⁶ .................................................. A47C 7/54
[52] U.S. Cl. .................................. 297/411.38; 248/276.1; 248/288.51; 297/411.33; 297/173
[58] Field of Search .......................... 297/411.32, 411.33, 297/411.35, 411.38, 188.21, 173; 248/118, 276.1, 288.51

[56] References Cited

U.S. PATENT DOCUMENTS

| | | | |
|---|---|---|---|
| 1,772,233 | 8/1930 | Vivier .................................... | 248/276.1 |
| 1,938,643 | 12/1933 | Smith .................................... | 248/276.1 |
| 3,910,538 | 10/1975 | Baitella ............................. | 248/276.1 X |
| 4,277,102 | 7/1981 | Aaras et al. ......................... | 248/118 X |
| 5,029,941 | 7/1991 | Twisselmann ...................... | 297/411.38 |
| 5,169,207 | 12/1992 | Rye ..................................... | 297/411.33 |
| 5,571,274 | 11/1996 | Holstensson ........................ | 297/411.38 |
| 5,582,464 | 12/1996 | Maymon ............................. | 297/173 X |

*Primary Examiner*—Peter M. Cuomo
*Assistant Examiner*—Stephen Vu
*Attorney, Agent, or Firm*—Jordan and Hamburg LLP

[57] ABSTRACT

An articulated holding arm 2 comprises a first arm 3 and a second arm 5. The first arm 3 is essentially cylindrical as a whole, and is provided with at an intermediate area but closer to a proximal end 6 of the arm 3 a first spherical element 7 in a freely rotatable manner. The first arm 3 is further provided with at a distal end 4 thereof to which the proximal end 6 of the arm 3 is mounted a second spherical element 8 in a freely rotatable manner. Provided between the first and second spherical elements 7,8 is a locking spindle 9 which is moveable in a longitudinal direction of the arm 3 with a very short interval d. Provided at a proximal end 6 of the first arm 3 is a piston 11 which constantly pressurizes via spring means 12 the first spherical element 7 in a direction of a tip of the piston 11 and can move the first spherical element 7 via hydraulic means 14 or pneumatic means toward the proximal end 6 of the first arm 3 against the spring means 12. The second arm 5 is provided with at a distal end 19 thereof a supporting element 20 for supporting an arm A of a person seated D.

10 Claims, 5 Drawing Sheets

BALANCING CHAIR

BACKGROUND OF THE INVENTION

The present invention relates to a balancing chair.

Brain surgeries and cardiac surgeries are nerve-exhausting and often require long hours of operation, for example, eight to nine hours. In brain surgery, for instance, an operating microscope is used to observe affected areas for operation, and the doctors are often required to keep his/her arm raised with an operating tool, such as a surgical knife, held in his/her hand and to keep such a position for hours. Such a long operation is a load both to patients and doctors physically and mentally. Such a trouble as mentioned above is common not only among medical doctors, but also among skilled technical workers who have to do handwork for hours with arm kept raised.

The present invention is designed from a viewpoint of the above matter, and it is an object of the invention to provide a balancing chair capable of relieving a physical load to those who have to work or operate with his/her arm kept raised.

SUMMARY OF THE INVENTION

In order to achieve the above object, the balancing chair according to the present invention supports an arm of a person seated by means of an articulated holding arm provided to a chair body and comprises a first arm mounted to the chair body, and a second arm mounted to a distal end of the first arm. The first arm is essentially cylindrical as a whole and is provided with, at an intermediate area nearer to a proximal end of the first arm, a first spherical element fixed to the chair body in a freely rotatable manner and is further provided with, at a distal end of the first arm, a second spherical element which is also freely rotatable and via which a proximal end of the second arm is mounted to a distal end of the first arm. Provided between the first spherical element and a second spherical element is a locking spindle moveable in a longitudinal direction thereof at a very short interval. Provided at a proximal end of the first arm is a piston which constantly pressurizes, via spring means, the first spherical element in a direction of the distal end of the first arm and can move the first spherical element, via hydraulic means or pneumatic means, toward the proximal end of the first arm against the spring means. The second arm is provided with, at a distal end thereof, a supporting element for supporting an arm of a person seated.

The articulated holding arm is basically freely rotatable about both the first spherical element fixedly provided to the chair body and the second spherical element provided between the first and second arms. However, in normal use, a spring means allows the piston to apply pressure to the first spherical element in a direction of the distal end of the first arm, so that the first spherical element pushes the locking spindle, consequently the locking spindle pushes the second spherical element. Resultantly, the first spherical element is securely sandwiched between the piston and the locking spindle, and the second spherical element is securely sandwiched between the locking spindle and the distal end, thereby locking the free rotation of both the first and second spherical elements. Resultantly, the whole articulated holding arm assumes a locked state to securely support an arm, more particularly the weight of the arm of a person seated. Thus, since the person seated no longer needs to support the weight of his/her own arm, physical load in a long-hour surgical operation or other work is minimized.

For free movement of the person's arm by releasing the locked state of the articulated holding arm, a hydraulic means or pneumatic means should be employed to move the piston toward a proximal end of the holding arm against the spring load. Consequently, the freely rotatable first and second spherical elements allow the whole articulated holding arm to be freely rotated about the first and second spherical elements.

The present invention is not limited to the above description, and its objects, advantages, features, and applications will become more apparent from the following description in conjunction with the accompanying drawings. It should be understood that changes and modifications are possible without departing from the spirit and scope of the invention.

DETAILED DESCRIPTION

Figure 1:
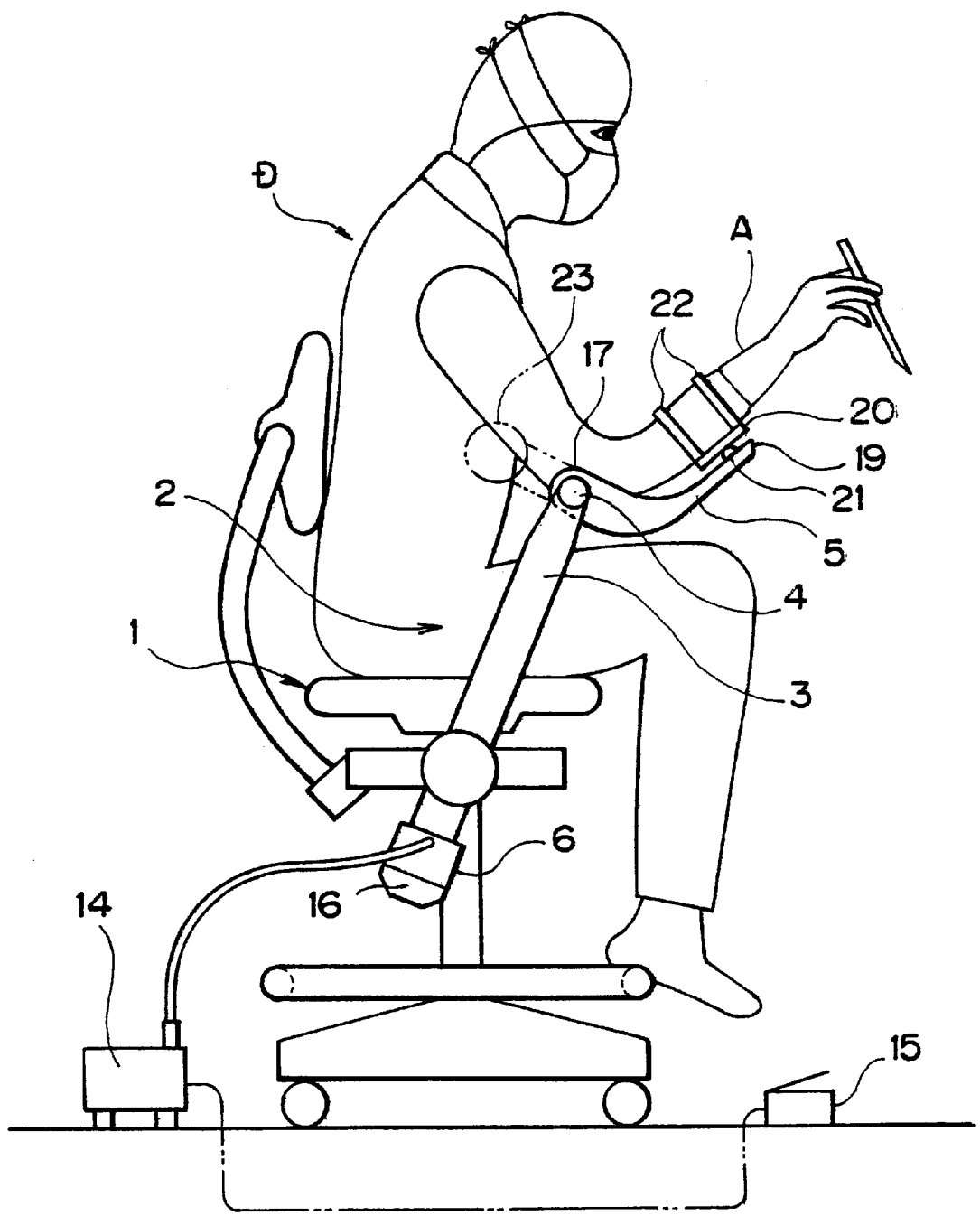
FIG. 1 is a side view of a balancing chair according to an embodiment of the present invention.

A preferred embodiment of the present invention will be described with reference to the accompanying drawings. Reference numeral 1 denotes a chair body to which an articulated holding arm 2 is mounted.

The articulated holding arm 2 comprises a first arm 3 mounted to the chair body 1 and a second arm 5 mounted to a distal end 4 of the first arm 3.

The first arm 3 is substantially cylindrical and is provided with, at an intermediate area nearer a proximal end 6 of the arm 3, a first spherical element 7 in a freely rotatable manner. The first spherical element 7 has a connecting portion 7a which outwardly protrudes. The first arm 3 is further provided with, at a distal end 4 thereof, a second spherical element 8 in a freely rotatable manner. The second spherical element 8 has a connecting portion 8a which also outwardly protrudes. The connecting portion 7a of the first spherical element 7 is fixed to the chair body 1. The distal end 4 has a top inner surface 4a which is shaped as an arc inner surface suitable to a surface of the second spherical element 8.

Figure 5:
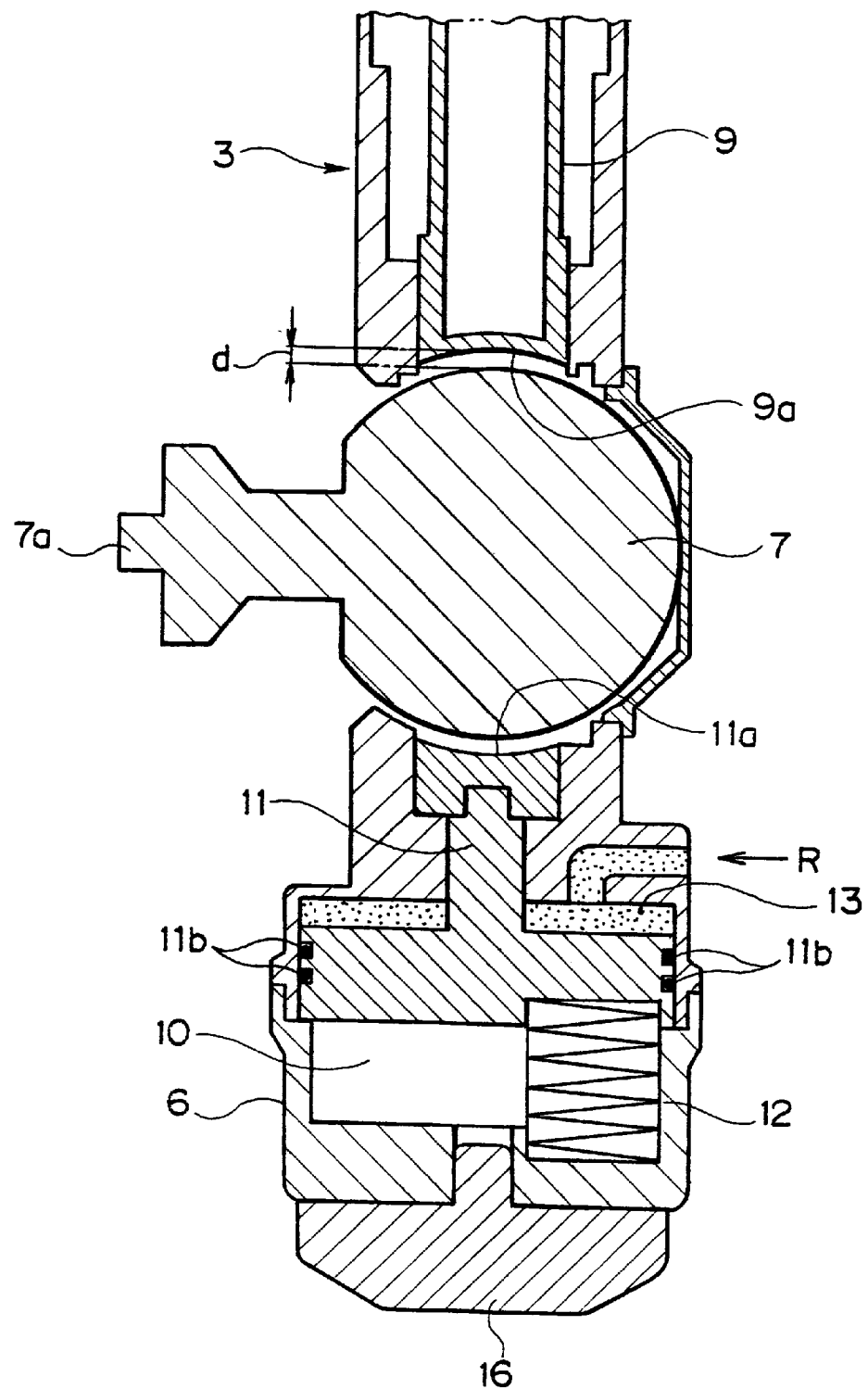
FIG. 5 is a cross-sectional view of a proximal end of the first arm illustrating a released state.

An interior cavity of the first arm 3 has a hollow locking spindle 9 provided between the first spherical element 7 and the second spherical element 8. The locking spindle 9 has at both ends thereof arc inner contact surfaces 9a,9b which are respectively shaped suitable to a surface of the first spherical element 7 and the second spherical element 8. The contact surfaces provide larger contact area when the locking spindle 9 and the surfaces of the first spherical element 7 and the second spherical element 8 contact, thereby producing sufficient frictional force. As shown in FIG. 5, a very short interval d is provided between the locking spindle 9 and first and second spherical elements 7, 8 and which allows the locking spindle 9 to move in longitudinal directions of the first arm 3 within a range of the interval d. It should be noted that FIG. 5 illustrates the very short interval d exaggerated. The interval d is sufficient to allow the first and second spherical elements 7, 8 to be rotated, but the contact surface 9a of the locking spindle 9 is positioned closer to the first spherical element 7 than the actually illustrated state for readily applying pressure to the first spherical element 7.

The arm 3 has a hollow proximal end 6 of which interior space 10 is provided with a piston 11. The piston 11 has, at an extremity thereof, a contact surface 11a formed as an arc inner surface which is suitable to the surface of the first spherical element 7. On a sliding surface between the piston 11 and the inner surface of the interior space 10, an O ring 11b is provided. The piston 11 is constantly urged in a direction toward the extremity by three coil springs 12 as a spring means disposed in a trigonal equiangular manner on a same plane, thus only one of the springs is shown in the drawings.

Formed between the piston 11 and the inner surface of the interior space 10 is a cylinder chamber 13 into which oil R is injected through a hydraulic pump 14 as a hydraulic means. The hydraulic pump 14 is optionally operated with a foot switch 15 installed near feet of a person such as a doctor seated D. Further, the proximal end 6 is provided with a counterweight 16.

On the other hand, a proximal end 17 of the second arm 5 is mounted to the connecting portion 8a of the second spherical element 8 provided on the distal end 4 of the first arm 3. The proximal end 17 is mounted via a screw 1 8 which allows the whole second arm 5 to be readily detached. In this sense, the detachable structure is useful for sterilizing the second arm 5.

Figure 2:
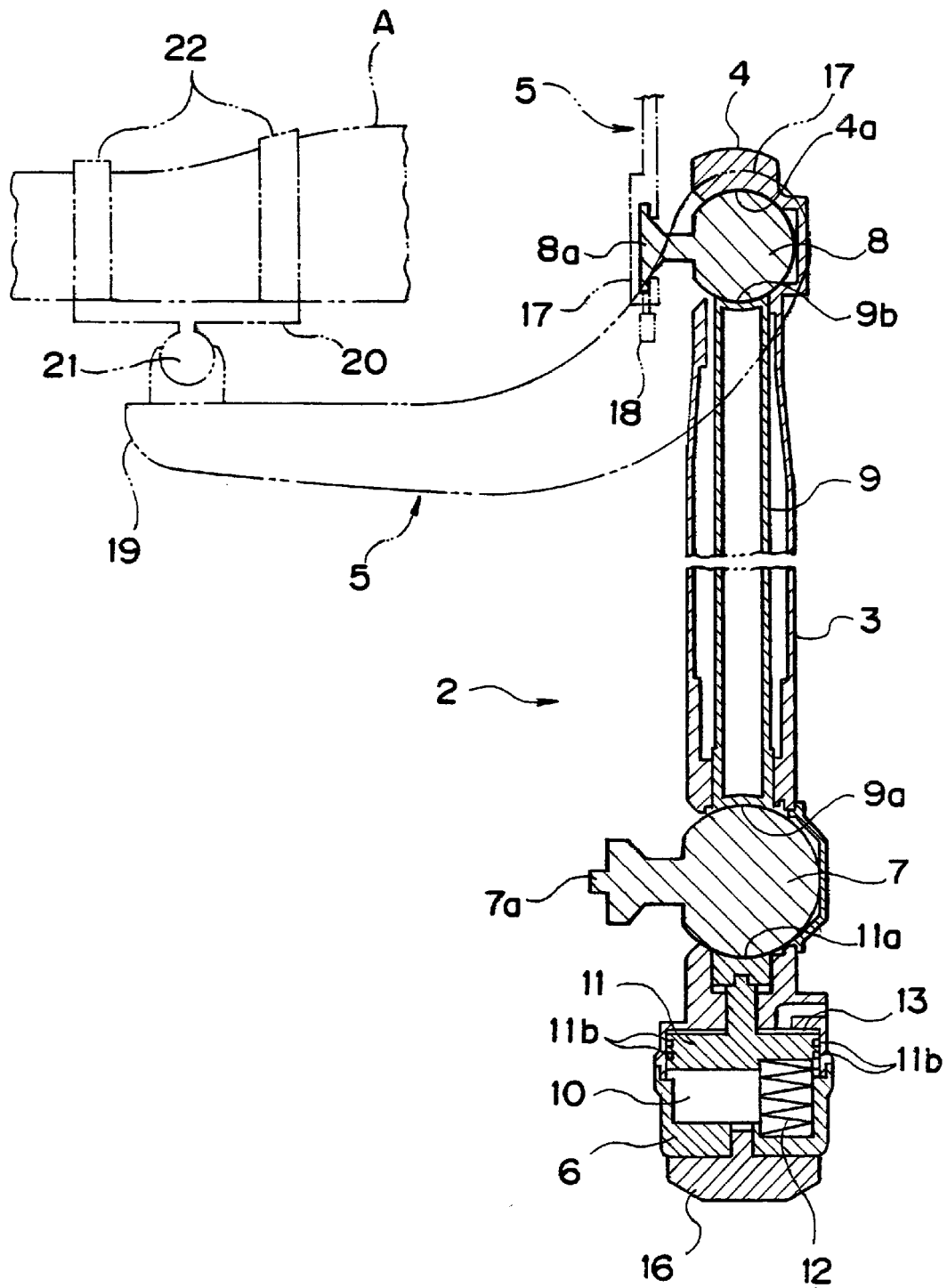
FIG. 2 is a cross-sectional view of a first arm.
Figure 3:
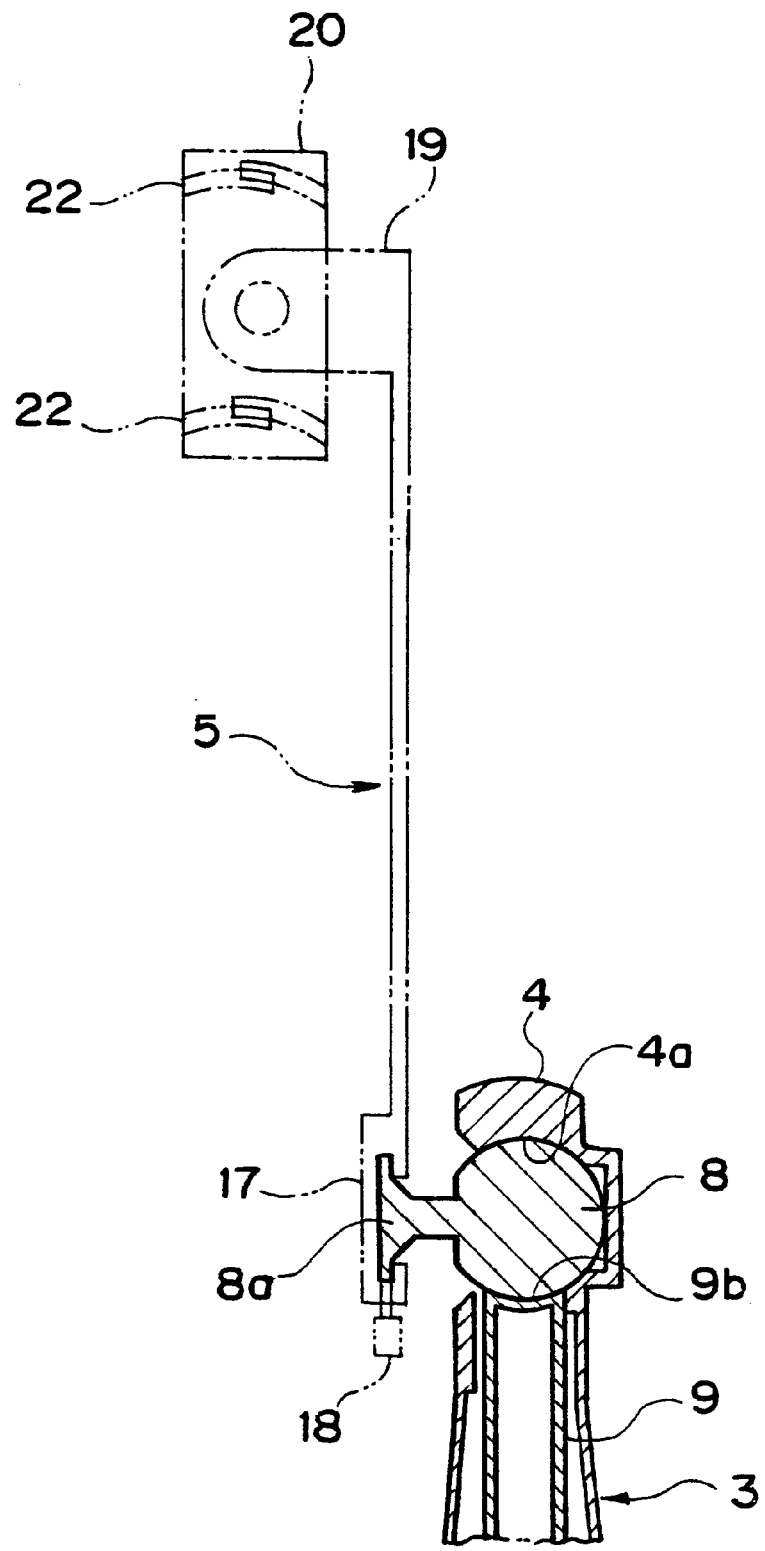
FIG. 3 is a cross-sectional view of a second arm.

The second arm 5 is formed as a curved lever of which extremity 19 is mounted with a plate-like supporting element 20 via a freely rotatable spherical element 21. The supporting element 20 is provided with a belt element 22 for fixing an arm A. Although an arm A is fixed in the belt element 22, a wrist and fingertips are movable thus presenting no trouble in a surgical operation or other works. It should be also noted that the second arm 5 and a supported arm A is illustrated with a two-dotted chain line in FIG. 2 as seen from two angles for better depicting the structure.

Figure 4:
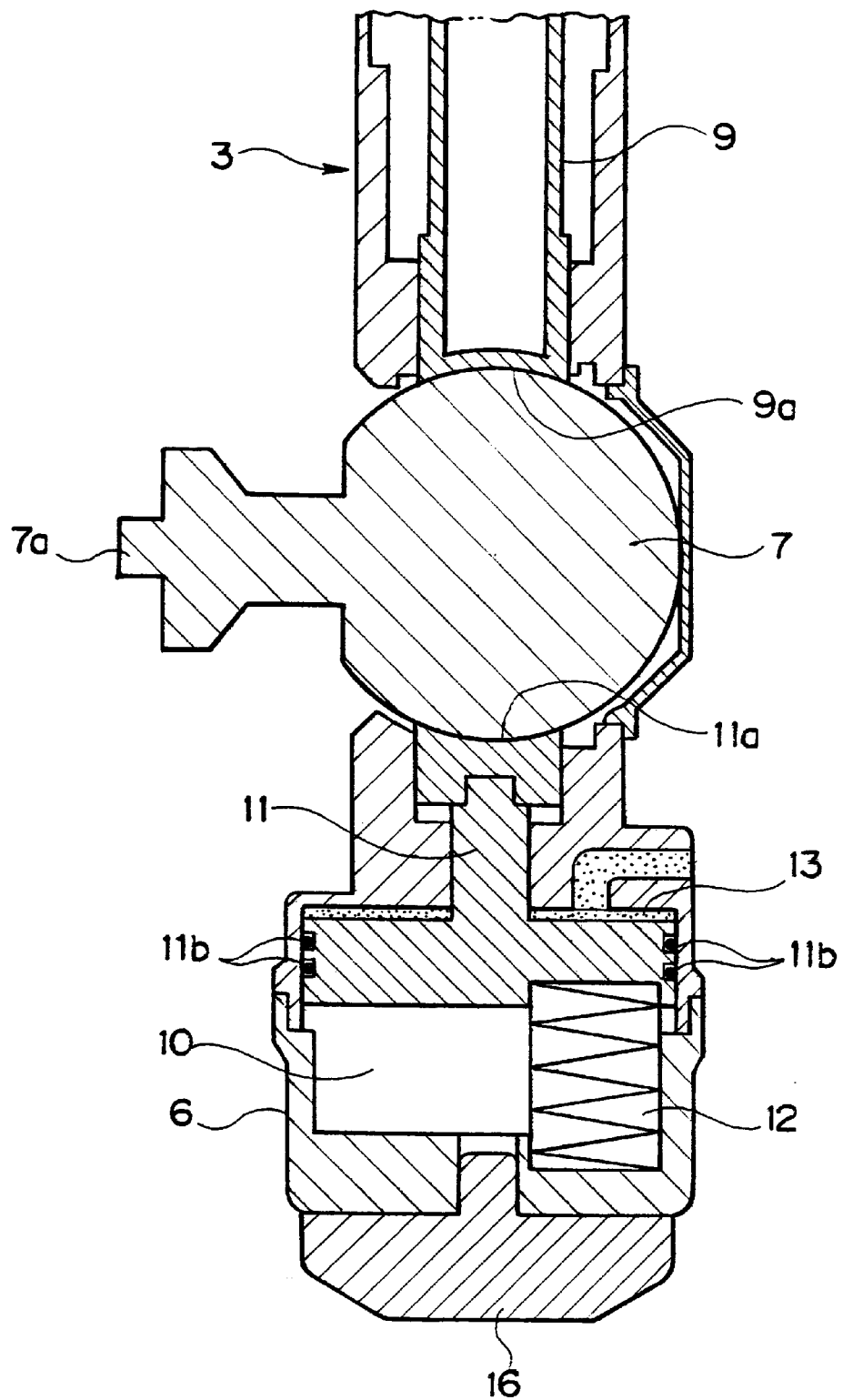
FIG. 4 is a cross-sectional view of a proximal end of the first arm illustrating a locked state.

Referring to FIG. 4, in normal use, a spring action of the coil spring 12 allows the piston 11 to press the first spherical element 7 in a direction of the distal end of the arm 3, so that the first spherical element 7 pushes the locking spindle 9, consequently the locking spindle 9 pushes the second spherical element 8. Resultantly, the first spherical element 7 is sandwiched between the piston 11 and the locking spindle 9, and the second spherical element 8 is sandwiched between the locking spindle 9 and the top inner surface 4a of the distal end 4, thereby locking the free rotation of both the first and second spherical elements 7,8. Resultantly, the whole articulated holding arm 2 assumes a locked state to securely support the arm A, more particularly the weight of the arm A of a person seated D. Thus, since the person seated D no longer needs to support the weight of his/her own arm A, physical load during a long surgical operation or other work will be minimized.

Referring to FIG. 5, for free movement of the arm A by releasing the locked state of the articulated holding arm 2, pressing the foot switch 15 will send oil R under pressure through the hydraulic pump 14 to cylinder chamber 13 to move the piston 11 toward the proximal end against the spring load. Consequently, the freely rotatable first and second spherical elements 7,8 allow the whole articulated holding arm 2 to be freely rotated. The articulated holding arm 2 is readily operated due to the counterweight 16 mounted to the proximal end 6. Another counterweight 23, if provided, as shown in FIG. 1, at the side of the proximal end 17 of the second arm 5 in addition to the counterweight 16 further permits easier operation.

The present invention is also applicable to, for example, operators who need to operate with his/her arm kept raised at a manufacturing line or assembly line in a factory, operate a keyboard with his/her arm kept raised, or persons whose arm's muscular strength have been lowered due to disease.

The articulated holding arm 2, according to the embodiment showing employs only a spring load and hydraulic pressure, namely eliminates an electric system, so that electric-related trouble does not occur and sterilizing treatment can be applied. The articulated holding arm 2 has a structure which assumes a locked state in normal use and a released state only when necessitated, so that the locked state is maintained if any trouble with a driving means occurs. The hydraulic means can be replaced by a pneumatic means.

The balancing chair according to the present invention is capable of supporting the weight of the arm A of a person seated and minimizes physical load even after a long operation or work. The balancing chair can follow any posture of a person seated, so that a surgical operation or other work will not be bothered.

What is claimed is:

1. A balancing chair for supporting an arm of a user comprising:

a chair body;

an articulated holding arm including a first arm having a first arm proximal end, a first arm distal end and an intermediate portion therebetween, and a second arm having a second arm proximal end and a second arm distal end;

said first arm defining an interior cavity having a first socket located at a intermediate portion of said first arm and a second socket located proximate said first arm distal end;

a first spherical element fixed to said chair body and rotatably engaged in said first socket of the first arm;

a second spherical element rotatably engaged in said second socket and fixed to said proximal end of said second arm;

a locking spindle slidably provided in said interior cavity of said first arm between said first spherical element and said second spherical element, said locking spindle having a length sufficient to simultaneously engage both said first spherical element and said second spherical element;

a compression means, in said interior cavity at said proximal end of said first arm, for compressing simultaneously said first spherical element into said locking spindle, to compress said first spherical element, and said locking spindle into said second spherical element, to compress said second spherical element, to lock positions of said first spherical element and said second spherical element in said first arm;

said compression means further having releasing means for permitting the user to selectively decompress said first spherical element, said locking spindle and said second spherical element to permit adjustment of positions of said first spherical element and said second spherical element relative to said first arm; and and said second arm having an arm support element at said distal end thereof for supporting the arm of the user.

2. A balancing chair for supporting an arm of a user comprising:

a chair body;

an articulated holding arm including a first arm having a first arm proximal end, a first arm distal end and an intermediate portion therebetween, and a second arm having a second arm proximal end and a second arm distal end;

said first arm defining an interior cavity having a first socket located at a intermediate portion of said first arm and a second socket located proximate said first arm distal end;

a first spherical element fixed to said chair body and rotatably engaged in said first socket of the first arm;

a second spherical element rotatably engaged in said second socket and fixed to said proximal end of said second arm;

a locking spindle slidably provided in said interior cavity of said first arm between said first spherical element and said second spherical element, said locking spindle having a length sufficient to simultaneously engage both said first spherical element and said second spherical element;

a compression means, in said interior cavity at said proximal end of said first arm, for compressing simultaneously said first spherical element into said locking spindle, to compress said first spherical element, and said locking spindle into said second spherical element, to compress said second spherical element, to lock positions of said first spherical element and said second spherical element in said first arm, and said compression means further having releasing means for permitting the user to selectively decompress said first spherical element, said locking spindle and said second spherical element to permit adjustment of positions of said first spherical element and said second spherical element relative to said first arm;

said second arm having an arm support element at said distal end thereof for supporting the arm of the user; and a counterweight at the proximal end of the first arm, said counterweight having a mass for counterbalance said first arm, said second arm and said arm support element about said first spherical element.

3. The balancing chair for supporting an arm of a user comprising:

a chair body;

an articulated holding arm including a first arm having a first arm proximal end, a first arm distal end and an intermediate portion therebetween, and a second arm having a second arm proximal end and a second arm distal end;

said first arm defining an interior cavity having a first socket located at a intermediate portion of said first arm and a second socket located proximate said first arm distal end;

a first spherical element fixed to said chair body and rotatably engaged in said first socket of the first arm;

a second spherical element rotatable engaged in said second socket and fixed to said proximal end of said second arm;

a locking spindle slidably provided in said interior cavity of said first arm between said first spherical element and said second spherical element, said locking spindle having a length sufficient to simultaneously engage both said first spherical element and said second spherical element;

a compression means in said interior cavity at said proximal end of said first arm, for compressing simultaneously said first spherical element into said locking spindle, to compress said first spherical element, and said locking spindle into said second spherical element, to compress said second spherical element, to lock positions of said first spherical element and said second spherical element in said first arm, and said compression means further having releasing means for permitting the user to selectively decompress said first spherical element, said locking spindle and said second spherical element to permit adjustment of positions of said first spherical element and said second spherical element relative to said first arm; and a supporting element, for supporting the arm, mounted to said distal end of said second arm via a free-rotatable spherical element, and the supporting element having a belt element for fixing the arm on the supporting element.

4. A balancing chair according to claim 1 wherein said second arm has a counterweight extending from the proximal end of the second arm for counterbalancing a mass of said second arm and said support element.

5. The balancing chair according to claim 1 wherein said compression means comprises:

said interior cavity defining a piston cylinder at said proximal end of said first arm;

a piston slidably disposed in said piston cylinder;

bias means for biasing said piston into said first spherical element to effect said compression;

said releasing means includes a pump for applying one of hydraulic and pneumatic pressure to said piston to overcome said biasing of said bias means.

6. The balancing chair of claim 5 wherein said bias means is at least one spring disposed to urge said piston toward said first spherical element.

7. The balancing chair of claim 6 wherein said pump is a foot operated pump.

8. The balancing chair according to claim 7 wherein a counterweight is provided at the proximal end of the first arm having a mass for countering a weight of said first arm on a side on an opposing side of said first socket and a weight of said second arm to ease pivoting of said first arm about said first spherical element.

9. The balancing chair of claim 5 wherein said pump is a foot operated pump.

10. The balancing chair according to claim 9 wherein a counterweight is provided at the proximal end of the first arm having a mass for countering a weight of said first arm on a side on an opposing side of said first socket and a weight of said second arm to ease pivoting of said first arm about said first spherical element.

\* \* \* \* \*